US00PP14270P29

(12) United States Plant Patent
Radler

(10) Patent No.: US PP14,270 P2
(45) Date of Patent: Nov. 4, 2003

(54) CLIMBING SHRUB ROSE PLANT NAMED 'RADRAMBLIN'

(50) Latin Name: *Rosa hybrida*
Varietal Denomination: Radramblin

(75) Inventor: William J. Radler, Greenfield, WI (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 10/152,572

(22) Filed: May 23, 2002

(51) Int. Cl.[7] ..... A01H 5/00

(52) U.S. Cl. ..... Plt./115
(58) Field of Search ..... Plt./115

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new and distinct variety of shrub rose plant is provided which forms in abundance on a continuous basis attractive clusters of fully double rich red blossoms. The vegetation is strong and vigorous. A compact climbing shrub growth habit is displayed. Attractive foliage is formed having a touch of red prior to maturing the deep dark green. Good tolerance to Black Spot and Powdery Mildew is exhibited. Attractive ornamentation is made possible on a trellis, fence or building with support.

1 Drawing Sheet

Figure 1:
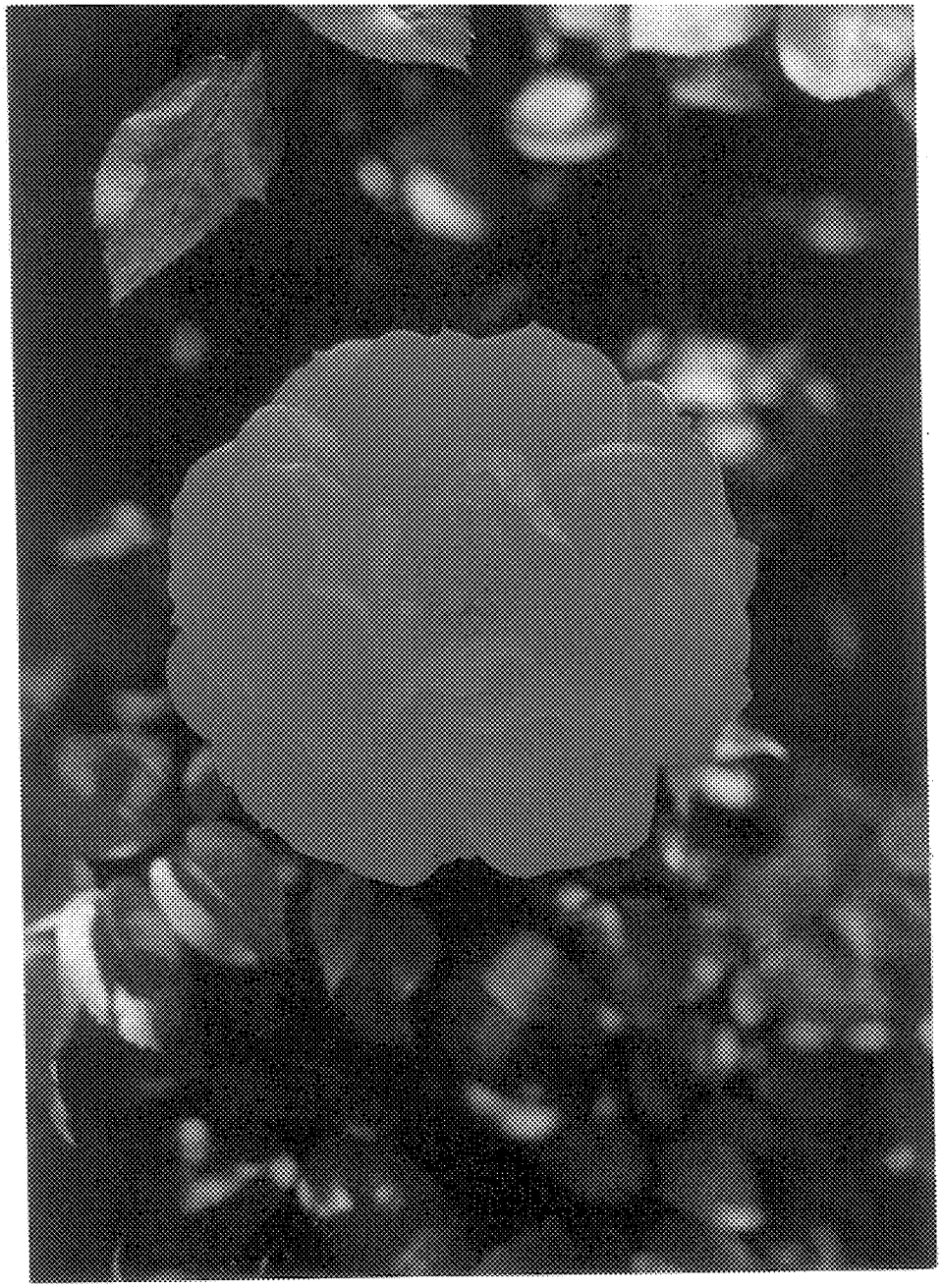

Botanical/commercial classification: *Rosa hybrida*/ Climbing Shrub Rose.
Varietal denomination: cv. 'Radramblin'.

SUMMARY OF THE INVENTION

The new variety of *Rosa hybrida* climbing shrub rose plant of the present invention was created by artificial pollination wherein two parents were crossed which previously had been studied in the hope that they would contribute the desired characteristics. The female parent (i.e., the seed parent) of the new variety was the 'Razzle' variety (non-patented in the United States). The male parent (i.e., the pollen parent) of the new variety was the 'Henry Kelsey' variety (non-patented in the United States). The 'Henry Kelsey' variety is a *Rosa kordesii* hybrid and a member of the Explorer Rose Series. The parentage of the new variety can be summarized as follows:

'Razzle'×'Henry Kelsey'

The seeds resulting from the above pollination were sown and small plants were obtained which were physically and biologically different from each other. Selective study resulted in the identification of a single plant of the new variety. This plant was initially designated 87-50-1.

It was found that the new variety of landscape shrub rose plant of the present invention possesses the following combination of characteristics:

(a) abundantly forms on a continuous basis attractive clusters of fully double rich red blossoms,
(b) exhibits a climbing shrub growth habit with strong long pliable stems,
(c) forms vigorous vegetation,
(d) forms attractive foliage having a touch of red prior to maturing to deep dark green,
(e) exhibits good winter hardiness, and
(f) exhibits good tolerance to Black Spot and Powdery Mildew.

The new variety well meets the needs of the horticultural industry. It can be grown to advantage as attractive ornamentation in parks, gardens, public areas, and residential landscapes. It is particularly well suited for growing as a single or multiple climber on a trellis, fence or building with support. The bright red blossoms contrast nicely with the deep dark green foliage that has a satin finish and fully serrate margins.

The characteristics of the new variety have been found to be homogeneous and stable and strictly transmissible at Yamhill, Oreg.; St. Paul, Minn.; and Phoenix, Ariz.; by asexual propagation such as by budding on 'Dr. Huey' understock and by the rooting of cuttings. The plant propagates well and grows very well on its own roots when propagated from cuttings.

The new variety can be readily distinguished from its parental varieties, and is considered to be an improved version of its 'Henry Kelsey' pollen parent. For instance, the fully double blossoms of the new variety are a richer truer red than those of the 'Henry Kelsey' variety and the foliage is satiny unlike the glossy foliage of the 'Henry Kelsey' variety.

The new variety has been named 'Radramblin'. The new variety is being marketed under the RAMBLIN RED trademark.

'Radramblin' has not been observed under all possible environmental conditions to date. Accordingly, it is possible that the phenotype may vary somewhat with variations in the environment, such as temperature, light, etc.

BRIEF DESCRIPTION OF THE PHOTOGRAPH

The accompanying FIG. 1 shows, as nearly true as it is reasonably possible to make the same in a color illustration of this character, a typical specimens of new variety. The photograph was prepared during the June 2000 while observing a two-year old plant of the new variety that was growing outdoors at St. Paul, Minn. Such plant had been propagated by the rooting of cuttings. A fully double rich red blossom and the attractive deep dark green deep satiny foliage are illustrated.

DETAILED DESCRIPTION

The chart used in the identification of colors is that of The Royal Horticultural Society (R.H.S. Colour Chart). The description is based on the observation of three year-old specimens the new variety during June and July 2001 while grown outdoors on their own roots at St. Paul, Minn.

Plant:

*Height.*—Approximately 1.8 to 2.8 m on average at the end of the growing season.

*Width.*—Approximately 90 cm on average at the end of the growing season.

*Habit.*—Climbing.

Branches:

*Color.*—Young stems: Yellow-Green Group 148C with highlights of Red Group 53A. Adult wood: Yellow-Green Group 147B with highlights of Greyed-Purple Group 187C.

*Thorns.*—Size: approximately 1 to 1.5 cm on average with some smaller prickles near the peduncle. Color: Greyed-Purple Group 184B.

Leaves:

*Stipules.*—Parallel with auricle facing outwards.

*Petioles.*—Upper surface: Green Group 139C with highlights of Greyed-Purple Group 187C and some prickles. Under surface: Yellow-Green Group 147B.

*Leaflets.*—Number: 3, 5, and 7 (most often). Shape: ovate with a rounded and oblique base and an acuminate tip. Margin: finely serrulate. Overall appearance: dense, deep green in coloration, and with a satiny finish. Color (young foliage): Upper surface: Greyed-Purple Group 187A to 187B with highlights of Yellow-Green Group 147B to 147C. Under surface: Greyed-Purple Group 187B. Color (adult foliage): Upper surface: deep dark green, Green Group 137A to 137C. Under surface: Yellow-Green Group 147C with highlights of Yellow-Green Group 148D.

Inflorescence:

*Number of flowers.*—Commonly approximately 4 to 6 in clusters per lateral stem.

*Peduncle.*—Medium green, Green Group 141C with some prickles, and approximately 3.5 cm in length on average.

*Sepals.*—Length: approximately 2.25 to 2.75 cm with some extensions. Upper surface: commonly between Green Group 143A and 143B in coloration. Under surface: commonly between Greyed-Purple Group 187B and 187C with some areas of White Group 155D and some pubescence.

*Buds.*—Shape: slender. Length: approximately 2.5 cm on average. Diameter: approximately 1.25 cm at the base on average. Size: small to medium. Color (when opening): Upper surface: Cardinal Red, Red Group 53A. Under surface: Cardinal Red, commonly between Red Group 53B and 53C.

*Flower.*—Form: fully double. Diameter: approximately 7.5 cm on average. Color (when opening begins): Upper surface: Cardinal Red, Red Group 53A. Under surface: Cardinal Red, between Red Group 53B and 53C. Color (when blooming): Upper surface: Cardinal Red, between Red Group 53A and 53B. Under surface: Cardinal Red, Red Group 53C with highlights of Red Group 53D. Color (at end of blooming): Upper surface: Spinel Red, Red Group 54A. Under surface: Nyron Rose, Red Group 55B with highlights of Red Group 55C. Fragrance: slightly spicy. Petal shape: wedge-shaped with a serrate edge. Petal number: approximately 35 on average. Lastingness: blossoms commonly last approximately 3 to 5 days on the plant depending upon environmental conditions such as temperature and sunlight. Stamen number: approximately 85 on average. Anthers: Greyed-Orange Group 163B in coloration. Filaments: Red Group 51B in coloration. Pistils: approximately 79 on average. Stigmas: Yellow Group 11A in coloration. Styles: Red Group 45B in coloration. Receptacle: round in configuration and separate and free. Hips: ovoid. Seeds: oval to round in shape, rugose at the apex with villose hairs, and Greyed-Orange 164C with highlights of Greyed-Orange Group 165B in coloration.

Development:

*Vegetation.*—Vigorous and strong.

*Blossoming.*—Abundant and continuous.

*Resistance to diseases.*—Highly tolerant to Black Spot and Powdery Mildew during observations to date.

*Hip formation.*—Hips are formed.

*Hardiness.*—Performs well in U.S.D.A. Hardiness Zone Nos. 3 to 7.

I claim:

1. A new and distinct variety of shrub rose plant characterized by the following combination of characteristics:

(a) abundantly forms on a continuous basis attractive clusters of fully double rich red blossoms, (b) exhibits a climbing shrub growth habit with long pliable stems, (c) forms vigorous vegetation, (d) forms attractive foliage having a touch of red prior to maturing to deep dark green, (e) exhibits good winter hardiness, and (f) exhibits good tolerance to Black Spot and Powdery Mildew;

substantially as herein shown and described.

* * * * *